United States Patent [19]

Macvicar et al.

[11] Patent Number: 5,215,095

[45] Date of Patent: Jun. 1, 1993

[54] OPTICAL IMAGING SYSTEM FOR NEUROSURGERY

[75] Inventors: Brian A. Macvicar; Timothy W. Watson; Daryl W. Hochman, all of Calgary, Canada

[73] Assignee: University Technologies International, Alberta, Canada

[21] Appl. No.: 565,454

[22] Filed: Aug. 10, 1990

[51] Int. Cl.$^5$ .................. A61B 6/00; G01N 21/66
[52] U.S. Cl. ........................... 128/665; 250/461.2
[58] Field of Search ............... 128/633, 634, 664, 665; 250/461.2; 350/320, 418; 356/39–41

[56] References Cited

U.S. PATENT DOCUMENTS

| | | |
|---|---|---|
| 4,223,680 | 9/1980 | Jobsis . |
| 4,417,591 | 11/1983 | Culver . |
| 4,472,732 | 9/1984 | Bennett et al. . |
| 4,556,057 | 12/1985 | Hiruma et al. . |
| 4,618,991 | 10/1986 | Tabata et al. . |
| 4,638,798 | 1/1987 | Shelden et al. . |
| 4,649,482 | 3/1987 | Raviv et al. . |
| 4,759,076 | 7/1988 | Tanaka et al. . |
| 4,773,097 | 9/1988 | Suzaki et al. . |
| 4,777,598 | 10/1988 | Kellar et al. . |
| 4,786,165 | 11/1988 | Yamamoto et al. . |
| 4,835,532 | 5/1989 | Fant . |
| 4,869,247 | 9/1989 | Howard, III et al. . |

OTHER PUBLICATIONS

"Optical Imaging of Neuronal Actvity", Physiological Reviews, vol. 68, No. 4, Oct. 1988, by Grinvald, et al., pp. 1285–1367.
"Basic Mechanisms Implicated in Surgical Treatments of Epilepsy" by Ojemann, George A., 1980, pp. 261–277.
"Functional Organization of Primate Visual Cortex Revealed by High Resolution Optical Imaging", Ts'O et al. pp. 417–420 Science, Jul. 27, 1990.
"Optical Imaging of Cortical Activity: Real-Time Imaging Using Extrinsic-signals and high resolution imaging based on sloe intrinsic-signals", pp. 543–559, Lieke et al; Annul. Rev. Physiol. 1989.
"Functional Architecture of Cortex Revealed by Optical Imaging of Intrinsic Signals", by Grinvald et al., *Nature*, Nov. 27, 1986, pp. 361–364.
"Voltage-Sensitive Dyes Reveal a Modular Organization in Monkey Striate Cortex" by Blasdel, et al, pp. 579–585, *Nature* Jun. 5, 1986.
"Optical Imaging of Neuronal Activity in the Visual Cortex", by Grinvald et al, pp. 117–136 *Neural Mechanisms of Visual Perception*.
"A Nonaliasing, Real-Time Spatial Transform Technique", by Karl M. Fant, Jan. 1986.
"Automated Registration of Dissimilar Images: Application to Medical Imagery", M. Herbin et al, pp. 77–89.

*Primary Examiner*—Lee S. Cohen
*Assistant Examiner*—Kevin Pontius
*Attorney, Agent, or Firm*—Burns, Doane, Swecker & Mathis

[57] ABSTRACT

In accordance with the present invention a method and apparatus are disclosed for real time imaging of functional activity in cortical areas of a mammalian brain using intrinsic signals. The present invention enables dynamic, on-line imaging of, for example, a human brain during neurosurgery to permit more accurate identification of dysfunctional cortical areas. Cortical areas are identified on the basis of stimulus evoked changes which occur in the optical properties of the brain so that real time localization of seizure (e.g., epileptic seizure) foci and functional mapping can be observed during neurosurgery. Areas of pathological tissue such as epileptic foci and tumors can thus be identified and removed during neurosurgery without damaging important functional areas in the cortex near the tissue.

38 Claims, 6 Drawing Sheets

OPTICAL IMAGING SYSTEM FOR NEUROSURGERY

BACKGROUND OF THE INVENTION

The present invention relates generally to the detection of cortical activity. More particularly, the present invention relates to optical imaging of cortical activity in, for example, a human brain to map areas of vital brain function and to distinguish normal and abnormal areas of the cortex during human neurosurgery.

Neurosurgery focuses primarily upon the complete removal of abnormal brain tissue. Ideally, the neurosurgeon would be able to localize areas of the cortex committed to specific neural functions (i.e., speech cortex, primary motor and sensory areas and so forth) as well as the boundaries of pathological or dysfunctional tissue.

Presently, electroencephalogram (EEG) techniques are used prior to and during surgery (often in conjunction with electrocorticography) to examine the human cortex for the purpose of identifying areas of brain function. Such techniques provide a direct measure of brain electrical activity, in contrast to positron emission topography (PET) scans which look at blood flow and metabolic changes in tissue and computerized axial tomography (CAT) scans which look at tissue density differences, and which are used only in preoperative evaluation of a patient.

EEG techniques typically involve placing an array of electrodes (e.g., 16 silver ball electrodes) upon a surface of the cortex. Although EEG techniques have achieved widespread use in the medical field, such techniques do not provide a map of cortical function in response to external stimuli. A modification of EEG techniques, cortical evoked potentials, can provide some functional mapping. However, this technique fails to provide high spatial resolution.

The most commonly employed method of intraoperative localization of cortical function involves direct electrical stimulation of the cortical surface. Direct cortical stimulation is used to evoke either observed motor responses from specific body parts, or in the awake patient, to generate perceived sensations or to interrupt motor speech output. However, the common direct application of a stimulating current to the cortex runs the risk of triggering seizure activity in the operating room. Because the surgeon has no way of knowing the actual extent of cortex stimulation during direct application of a stimulating current, the extent of the brain tissue associated with a given function is also uncertain.

One limit of EEG techniques is that the size of and the distance between electrodes used to form an EEG array are relatively large with respect to the size of brain cells which compose brain tissue. The electrodes associated with a given cortical area therefore often encompass brain cells associated with more than one functional activity. Consequently, the cortical area of the brain which is producing electrical energy detected by a given electrode of the EEG array cannot be identified with specificity. A greater surface area of a cortex being examined is therefore associated with the control of a stimulated portion of a patient's body.

Such inaccuracies can have a dramatic impact when, for example, EEG techniques are used during brain surgery to treat neurological defects such as intractable epilepsy (i.e., epilepsy which can not be treated with medication). Using EEG techniques to identify a portion of the cortex responsible for the epileptic seizure can, and often does, result in a greater amount of cortical tissue removal than would be necessary to treat the epilepsy.

Despite recognition of the aforementioned inaccuracies, the over-inclusiveness of EEG techniques in identifying neurologically dysfunctional cortical areas has nevertheless been deemed acceptable treatment for disorders such as intractable epilepsy. It would therefore be desirable to provide a tool for neurosurgery which would significantly enhance the resolution of cortical activity mapping.

For a number of years, studies have been performed to identify more precise techniques for mapping cortical activity in mammals. One such study is described in an article by Gary G. Blasdel and Guy Salama entitled "Voltage-sensitive dyes reveal a modular organization in working striate cortex", *Nature International Weekly Journal of Science*, Vol. 321, No. 6070, Jun. 5, 1986, pp. 579–585. The study described by Blasdel et al. is directed to the use of voltage-sensitive dyes for optically imaging neuronal activity in the striate cortex of a monkey. Generally, the study describes identifying patterns of ocular dominance and orientation selectivity (related to the monkey's vision) by examining large areas of striate cortex known to correspond with the central and parafoveal portion of the monkey's visual field.

While these techniques may provide greater resolution in mapping cortical areas of functional activity, staining the exposed cortex with a voltage sensitive dye represents a relatively high level of intrusion to the cortex. The likelihood that such techniques would receive widespread acceptance for mapping in vivo mammalian brains is therefore rather limited.

Another study which is directed to optical imaging of cortical activity has been described, for example, in an article entitled "Functional architecture of cortex revealed by optical imaging of intrinsic signals,", by Amiram Grinvald, et al, *Nature*, Vol. 324, Nov. 27, 1986, pp. 361–364. As recognized by Grinvald et al., optical imaging of cortical activity offers advantages over conventional electrophysiological and anatomical techniques. The Grinvald study broadly describes a technique of optically imaging cortical activity using some intrinsic changes in the optical properties of mammalian brain tissue in response to electrical or metabolic activity. As noted in the Grinvald et al. article, intrinsic changes in brain tissue due to electrical or metabolic activity, often referred to as intrinsic signals, can be detected using reflection measurements without the use of the aforedescribed voltage sensitive dyes.

As described in an article "Optical Imaging of Cortical Activity: Real-time imaging using extrinsic dye-signals and high resolution imaging based on slow intrinsic signals", *Annu. Rev. Physiol.*, Lieke, Edmund E., et al., 1989, pp. 51:543.9, intrinsic signals are generally considered to be those changes which occur in the light reflecting properties of brain tissue due to activity in the nerve cells of the brain. There are basically two recognized components of the intrinsic signal. A first component is the change in absorption of light having wavelengths between 500–700 nm due to increased blood flow into an area of intense neuronal activity. The increased blood flow results in increased light absorption by hemoglobin at these wavelengths. A second component involves a change in light absorption at wavelengths in the near infrared region of the spectrum (i.e., above 800 nm) and is also associated with the occurrence of neuronal activity. This second component of the intrinsic signal appears to be due to a combination of movement of ions and water from the extracellular space into neurons, swelling of the cells, shrinkage of the extracellular space and neurotransmitter release.

While the Grinvald et al. article recognizes the advantages of using intrinsic signals to provide a non-intrusive method of imaging the barrel areas of a rat somatosensory cortex, each barrel area responding to stimulation of a single mystacial whisker of the rat, this study does not describe how the imaging technique described could, for example, be applied to real time imaging of a mammalian brain cortex. Because the rise time of a reflected light signal indicative of an intrinsic signal is recognized by Grinvald et al. as being slower than dye related signals, the usefulness of the optical imaging as described therein for real time analysis during surgery to remove a cortical area would appear limited.

In an article entitled "Functional Organization of Primate Visual Cortex Revealed by High Resolution Optical Imaging", Ts'O et al., *Science*, Vol. 249, pp. 417-420, a charge-coupled device (CCD) camera is disclosed for detecting intrinsic signals of the living monkey striate. However, imaging of a limited striate area in response to intrinsic signals is described as having been achieved via a relatively intrusive technique whereby a stainless steel optical chamber having a glass cover plate and being filled with silicon oil was cemented into a hole of the monkey's skull (see footnote 18, p. 420). Further, adequate cortical images are described as having been obtained by averaging over a 30 minute period to a 45 minute period (see footnote 22 on p. 420).

The foregoing studies relate to functional activities of the cortex and have been useful in furthering knowledge regarding complex function of a mammalian brain. However, these studies do not, for example, specifically address the inaccuracies of current EEG techniques or the development of systems and strategies for assisting in the real time, in vivo imaging of a human cortex to more accurately identify dysfunctional cortical areas during neurosurgery.

Accordingly, there is a need in the prior art for a non-intrusive system and method whereby optical imaging can be used to dynamically map cortical activity and thus precisely distinguish abnormal and normal cortical areas of, for example, the human brain during neurosurgery.

SUMMARY OF THE INVENTION

In accordance with the present invention, a method and apparatus are disclosed for real time imaging of functional activity in cortical areas of a mammalian brain using intrinsic signals. The present invention enables dynamic, on-line imaging of, for example, a human brain during neurosurgery to permit more accurate identification of dysfunctional cortical areas. Cortical areas are identified on the basis of stimulus evoked changes which occur in the optical properties of the brain so that real time localization of seizure (e.g., epileptic seizure) foci and functional mapping can be observed during neurosurgery. Specific areas of pathological tissue such as epileptic foci and tumors can thus be precisely identified and removed during neurosurgery without damaging important functional areas in the cortex near the tissue.

In accordance with exemplary embodiments of the present invention, rapid non-intrusive imaging of neuronal activity in a mammal brain is achieved with high resolution. For example, a difference image used to highlight changes in neuronal activity is obtained by comparing images corresponding to stimulated and post-stimulated conditions of the cortex with images corresponding to unstimulated conditions of the cortex. The difference image is enhanced by geometrically transforming the images from which it is generated. In addition, specialized imaging techniques can be employed to further enhance the difference images. Because the present invention enables intrinsic signals indicative of neuronal activity to be imaged in real time, dysfunctional cortical areas can be precisely identified during neurosurgery.

BRIEF DESCRIPTION OF THE DRAWINGS

Other objects and advantages of the present invention will become more apparent from the following detailed description of preferred embodiments as described with reference to the drawings wherein.

DETAILED DESCRIPTION OF THE INVENTION AND EMBODIMENTS THEREOF

In the following description of preferred embodiments of the invention, particular reference will be made to methods and apparatuses for optically imaging neuronal activity of in vivo cortical areas of humans being treated for neurological disorders such as intractable epilepsy. However, it will be appreciated by those skilled in the art that the present invention is not limited to such treatment, but can be equally applied to the imaging of any mammalian brain for the identification of cortical areas presently engaged in neuronal activity, which neuronal activity is manifested by the generation of intrinsic signals.

For purposes of the present invention, intrinsic signals are those signals which are indicative of intrinsic changes in cells, such as brain cells, due to neuronal activity. Such changes are, for example, generated in response to increased blood flow or ion and water movement in cells associated with cortical areas presently engaged in intense neuronal activity. However, it will be apparent to those skilled in the art that any changes which occur in cellular tissue as a result of neuronal activity and which produce a detectable change in reflective properties of the tissue, can serve as the intrinsic signals to be detected for purposes of the present invention.

Figure 1:
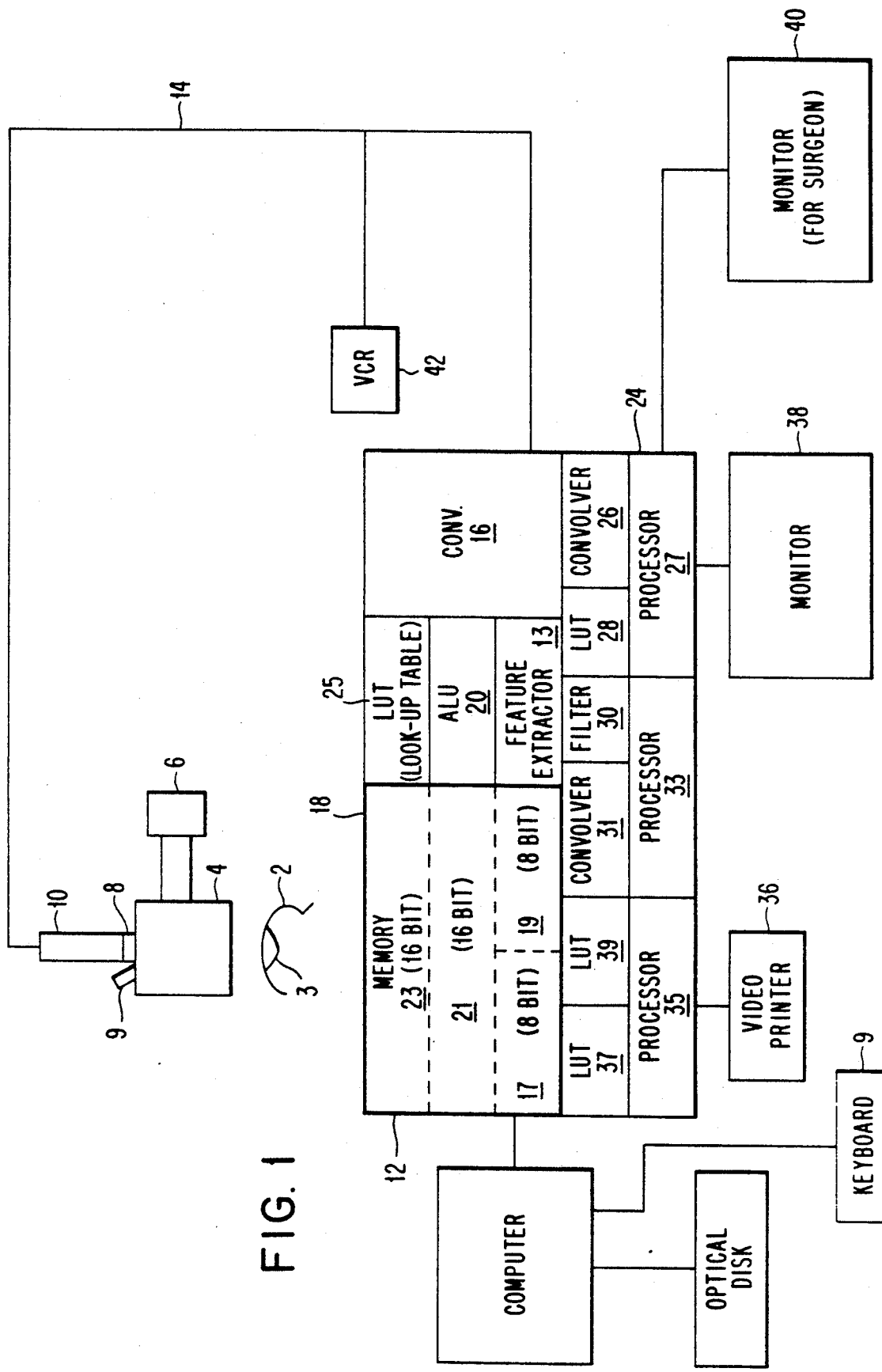
FIG. 1 is a block diagram of an exemplary system designed in accordance with the present invention.

FIG. 1 shows a preferred embodiment of a system designed in accordance with the present invention. In FIG. 1, a human brain 2 of a patient undergoing neurosurgery is shown. The brain 2 includes a cortical area which has previously been exposed by removing a portion of the patient's skull in the general area which is to be functionally mapped or which is believed to encompass dysfunctional brain tissue. In accordance with the present invention, an operating microscope 4 is provided, and includes a magnification lens which is focused on the exposed cortical area, represented by the area 3 of the brain 2. An illuminating means such as a regulated light source 6 is provided with the operating microscope to illuminate the exposed cortical area of the brain under consideration. A light filter 8 is also provided on a viewing side of the operating microscope's magnification lens to selectively pass reflected light from the cortical area of a given wavelength or wavelengths. The reflected light which passes through the light filter 8 is used to detect intrinsic changes in the brain tissue of the exposed cortical area being observed.

It will be appreciated by those skilled in the art that the operating microscope 4, the regulated light source 6 and the light filter 8 could be formed individually or could be formed as part of a single unit. Indeed, in a preferred embodiment, the operating microscope includes a filter and light source. One example of such a device is the fiber-optic illumination "Operation Microscope OPMI 1 FC", a product of the West German company Zeiss. Such a microscope provides magnifications of, for example, 12.5:1, 16:1 and 20:1 and provides a variable focal length and field of view. The regulated light source includes, for example, a Zeiss model 394031, 12 volt, 100 watt stabilized power supply.

The magnification, objective focal length and field of view may be selected to provide the desired resolution of a cortical area being viewed. However, an exemplary embodiment of the present invention can be implemented using a lens which provides a base 12.5:1 magnification with a 200 mm objective focal length, to provide a field of view diameter which varies from 50 mm to 8.0 mm (corresponding to a magnification range of from 4.0 to 25, respectively). A beamsplitter is provided in the microscope to permit connection of a light detecting means (such as a camera) to the microscope via a screw attachment, such as a C-mount and camera tube eyepiece. The camera tube eyepiece includes a lens having, for example, a focal length of 160 mm.

An image received by the camera tube eyepiece is transmitted to the light filter 8. The other image provided by the beamsplitter may be directed to a straight tube eyepiece 9, also having a tube focal length of 160 mm, for direct viewing by the surgeon of the cortical area being observed.

Reflected light from the cortical area which passes through the light filter 8 is received by the light detecting means 10. In an exemplary embodiment of the present invention, the light filter 8 permits only light in a wavelength range of approximately 800 nm±10 nm (i.e., near infrared) to pass to the light detecting means, this relatively longer wavelength range having been determined to provide accurate detection of neuronal activity deeper within the cortex (e.g., several hundred microns deep). Further, with a longer wavelength, less obscuring of brain tissue by the vasculature appears to occur.

It will be appreciated by those skilled in the art, however, that other wavelength ranges could be used to permit detection of neuronal activity to different depths of the cortex surface as well as detection of vasculature in the cortex. For example, using a wavelength in a range centered at 500 nm permits accurate detection of vasculature and neuronal activity closer to the cortex surface. Detection of vasculature permits, for example, the sensing of alterations in blood flow through the cortex during surgery to address problems associated with aneurysms. Further, use of the light filter 8 could be avoided altogether, as reflected white light has been determined to provide a detectable signal of neuronal activity.

In an exemplary embodiment of the present invention, the light detecting means 10 is a CCD video camera which outputs an analog video signal. For example, the video camera 10 can be a "CCD-72 Series Solid State Camera", a product of Dage-MTI Inc., of Michigan City, Ind. The video camera provides an analog signal having 512 horizontal lines per frame, each line containing video and timing information in known fashion using, for example, standard RS 170/330 conventions.

The analog video signal of the video camera 10 is continuously input to a means for acquiring and analyzing data, such as an image analyzer 12 via an input line 14. The image analyzer 12 is controlled by a computer 8 having an associated keyboard input 9. In an exemplary embodiment of the FIG. 1 system, the image analyzer 12 is, for example, a "Series 151 Image Processor" produced by Imaging Technology Inc. of Woburn, Mass., and described in the "Series 151 Reference Manual (47-H15101-01)" and the "Series 151 Programmer's Manual 47-S15001-01", published by Imaging Technology Inc., Technical Publications Dept., 600 W. Cummings Park, Woburn, Mass., 01801, 1986, the disclosures of which are hereby incorporated by reference in their entirety. As described therein, the Series 151 image processor includes a private video bus for transferring digitized video signals between component modules used to form the image analyzer.

More specifically, the image analyzer receives and digitizes an analog video signal output by the video camera 10 into frames of data. For this purpose, the image analyzer 12 includes an analog-to-digital (A/D) interface 16, such as the ADI-150 described in the aforementioned "Series 151 Reference Manual", for interfacing the analog video signal from the video camera 10 with the image analyzer 12. Digitization of the analog video signal from the video camera is performed at a frame frequency of 1/30th of a second.

In a preferred embodiment, a programmable look-up table is also included with the A/D interface and is initialized with values for converting grey coded pixel values representative of a black and white image to color coded values based on the intensity of each grey coded value in a manner to be described more fully below. Further, while described as being included in the image analyzer 12, it will be appreciated by those skilled in the art that the A/D interface could equally be provided as a separate module in the FIG. 1 embodiment, as could any of the modules to be described in connection with the image analyzer 12.

Each image received by the A/D interface is stored as a frame of data elements represented as a 512 by 512 array of pixels. However, only 480 lines of the array are used for actual image data to correspond with conventional monitor screen size. Digitization of the analog video signal results in each pixel of the 480 by 512 image array having an 8-bit value corresponding to one of 256 grey levels.

The image analyzer further includes a frame buffer 18 having three frame storage areas 17, 19 and 21, such as the FB-150 described in the aforementioned "Series 151 Reference Manual", for storing frames of digitized image data received from the A/D interface. The frame buffer is composed of at least one megabyte of memory space and includes, for example, at least one 512 by 512 16-bit frame storage area 17 (to store pixel intensities represented by more than 8 bits) and two 512 by 512 8-bit frame storage areas 19 and 21. In addition, a 16-bit frame storage area 23 may be provided as an accumulator for storing processed image frames having pixel intensities represented by more than 8 bits.

An arithmetic logic unit (ALU) 20 is included in the image analyzer for performing mathematical (e.g. add, subtract, etc.) and logical (e.g., "AND", "OR", etc.) functions. In the FIG. 1 embodiment the ALU is, for example, the ALU-150 Pipeline Processor described in the aforementioned "Series 151 Reference Manual", which maintains 16-bit accuracy throughout the pipeline. The ALU includes two sets of programmable look-up tables (LUT's) 25 each having 256 8-bit registers for performing point processing on output pixels from the frame buffer. More specifically, as will be described in connection with FIG. 2, the look-up tables included in the ALU can be used for performing thresholding and image compression operations.

An image analyzer for use with an exemplary embodiment of the present invention also includes means 13 for establishing a histogram of difference frames to enhance a resultant image generated by comparing two or more image frames. In an exemplary embodiment wherein the aforedescribed Imaging Technology Inc. Series 151 image processor is used, a "Histogram/Feature Extractor HF 151-1-V" module, available from Imaging Technology Inc. can be used to establish such a histogram during an on-line, live analysis embodiment of the present invention to be described more fully in conjunction with FIG. 3.

While the foregoing modules of the Series 151 image processor are adequate to implement an exemplary embodiment of both post-acquisition analysis and on-line analysis of image data, a more preferred embodiment of the present invention can, for example, be implemented by adding an optional real time processor 24 to provide enhanced pipeline processing speed. For example, in the aforedescribed exemplary embodiment which uses an Imaging Technology Inc. Series 151 image processor, real time modular processors could be added to the system. One such real time modular processor for use with the Series 151 image processor is the "150 RTMP-150 Real Time Modular Processor" described in the "RTMP-150 Reference Manual 47-HS15010-00" and the "Basic RTMP Programmer's Manual 47-S15010-00", both available from Imaging Technology Inc., Technical Publications Dept., 600 W. Cummings Park, Woburn, Mass., 01801, 1989, the disclosures of which are hereby incorporated by reference in their entirety.

Each real time modular processor includes a bus for interconnecting desired modules for use with the image processor. Accordingly, in accordance with the present invention, a real time sobel and convolver module 26, such as the Imaging Technology Inc. "CM150 RTS", which is described in the Imaging Technology manual "CM150 RTS 47-S15013-00", May 1989, can be used in conjunction with a first real time modular processor 27 for performing real time convolutions and filtering (e.g., fast Fourier transforms). More specifically, in an exemplary embodiment, the real time sobel and convolver 26 is used to perform a neighborhood averaging operation as will be described in conjunction with FIG. 3. A second real time sobel and convolver 31 is also provided in an exemplary embodiment to provide additional filtering without affecting processing speed of the pipeline. The second real time sobel and convolver is, for example, controlled by a second real time modular processor 33 to provide a second neighborhood averaging operation at a point further along in the pipeline processing of the real time processor 24.

In accordance with the present invention, a programmable look-up table 28, such as the "CM150-LUT16" of Imaging Technology, which is described in the Imaging Technology manual "CM150 LUT16 Software Manual 47-S15015-00", May 1989, can also be used in conjunction with the first real time modular processor 27 for performing the thresholding operation previously performed by one of the ALU look-up tables in the aforementioned post-acquision analysis embodiment.

A rank value filter 30 such as the "CM150 RVF8" of Imaging Technology Inc., which is described in the Imaging Technology manual "CM150 RVF8 47-S15012-00", May 1989, is further provided in an exemplary embodiment. In an exemplary embodiment, the rank value filter shares the second real time modular processor 33 with the second real time sobel and convolver, and enables real time median filtering of a digital image.

Median filtering refers to a known image processing technique whereby the digital values used to represent the intensity of the pixels in a given area of interest defined by a kernal (e.g., 3 by 3 pixel kernal) are sorted by rank (e.g., lowest intensity value to highest intensity value) to identify a median value. Because a kernal having an odd number of pixels is generally selected, the medium value will correspond to the pixel intensity ranked in the middle of the sorted intensity values (e.g., if the intensity value associated with pixels in a 3 by 3 kernal are 0,0,0,1,50,50,50,50 and 50, 50 would be the median value). The center pixel of the kernal is subsequently assigned a digital value corresponding to the median value while all other pixels retain their original digital value.

Afterwards the kernal is shifted one row or column and another median value selected for the center pixel of the kernal. This process is repeated until the entire image frame is processed. Such a technique is effective for further reducing noise present in the resultant digital image.

The exemplary embodiment of the present invention as depicted in FIG. 1 further includes a third real time modular processor 35 for controlling two additional look-up tables 37 and 39. The programmable look-up table 37 provides, for example, image enhancement via an image stretch. An image stretch corresponds to a known technique wherein the highest and lowest pixel intensity values used to represent each of the pixels in a digital image frame are determined over a region of the image frame which is to be stretched. Stretching a selected region over a larger range of values permits, for example, easier identification and removal of relatively high, spurious values due to noise, such as glare. The programmable look-up table 39 is used to provide the image compression operation previously performed by the programmable look-up table included in the ALU during the aforementioned post-acquisition analysis embodiment of the present invention. Thus, with the on-line, live analysis embodiment of the present invention, look-up tables included in the real time processor 24 perform the functions previously executed by the ALU look-up tables and thus further enhance processing speed. The function of these additional look-up tables will be further described below in connection with the on-line, live analysis of FIG. 3.

In yet another alternate embodiment of the present invention, a binary correlator (not shown) such as the Imaging Technology Inc. "CM150 BC32", as described in the "CM150 BC32 Software Manual 47-S15014-00" published by Imaging Technology Inc., can be further included in the real time processor 24 for performing a real time comparison of pixel values. In such an embodiment of the present invention, the binary correlator 32 would, for example, execute a one-to-one comparison of the pixel values composing two digital images, and produce an output only when a difference between the pixel values exists thus forming a frame of subtracted pixel values.

The computer used to control the image analyzer 12 can be any known portable computer which is properly interfaced to the image analyzer for transferring control signals thereto and for receiving data therefrom. In exemplary embodiments, the computer 8 is an "IBM Personal Computer AT (PC AT)" (a product of IBM Corp.) or a Zenith 386 personal computer.

The FIG. 1 system also includes an optical disk 34 for storing digital image data, a video printer 36 for providing a hard copy of a digital and/or analog image from the video camera, and two monitors 38 and 40 for viewing a digital and/or analog image from the video camera. In a preferred embodiment, the monitors 38 and 40 are capable of simultaneously displaying both a digital difference frame image from the image analyzer 12 and an averaged image frame obtained from the video camera 10, with the digital difference frame image being superimposed on the averaged image frame output obtained from the video camera. A video tape recorder (VCR) 42 is further provided for recording ongoing analog outputs of the video camera or images displayed on the monitors 38 and 40 for later reference.

The operation of the FIG. 1 system will now be described in conjunction with the flow charts of FIGS. 2 through 5. In a first exemplary embodiment to be described in conjunction with the FIG. 2 flow chart, an image acquisition and storage operation will be described wherein post acquisition analysis of the data is performed. In this embodiment, the additional processing power provided by the real time modular processor and its associated modules as described above is optional, and an image analyzer such as the Imaging Technology Inc. Series 151 image processor provides satisfactory results.

Figure 3:
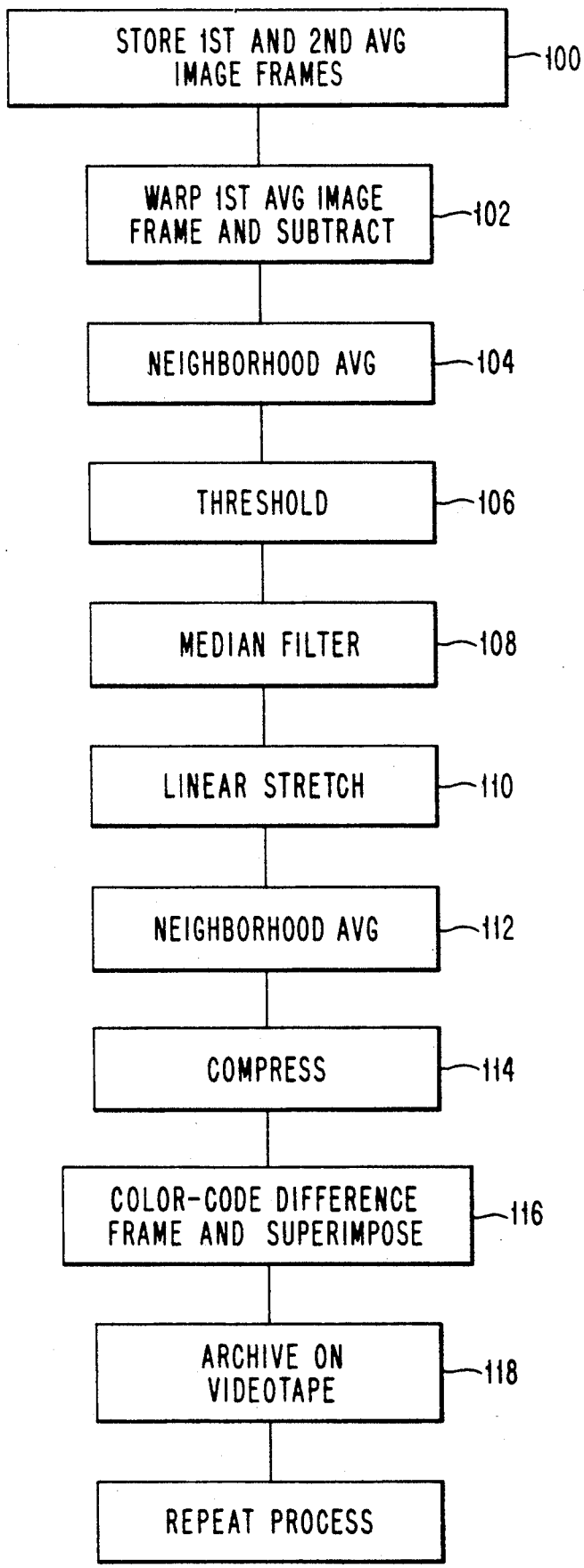
FIG. 3 is a flow chart illustrating an exemplary method for implementing the present invention in an on-line, live image analysis mode.
Figure 4:
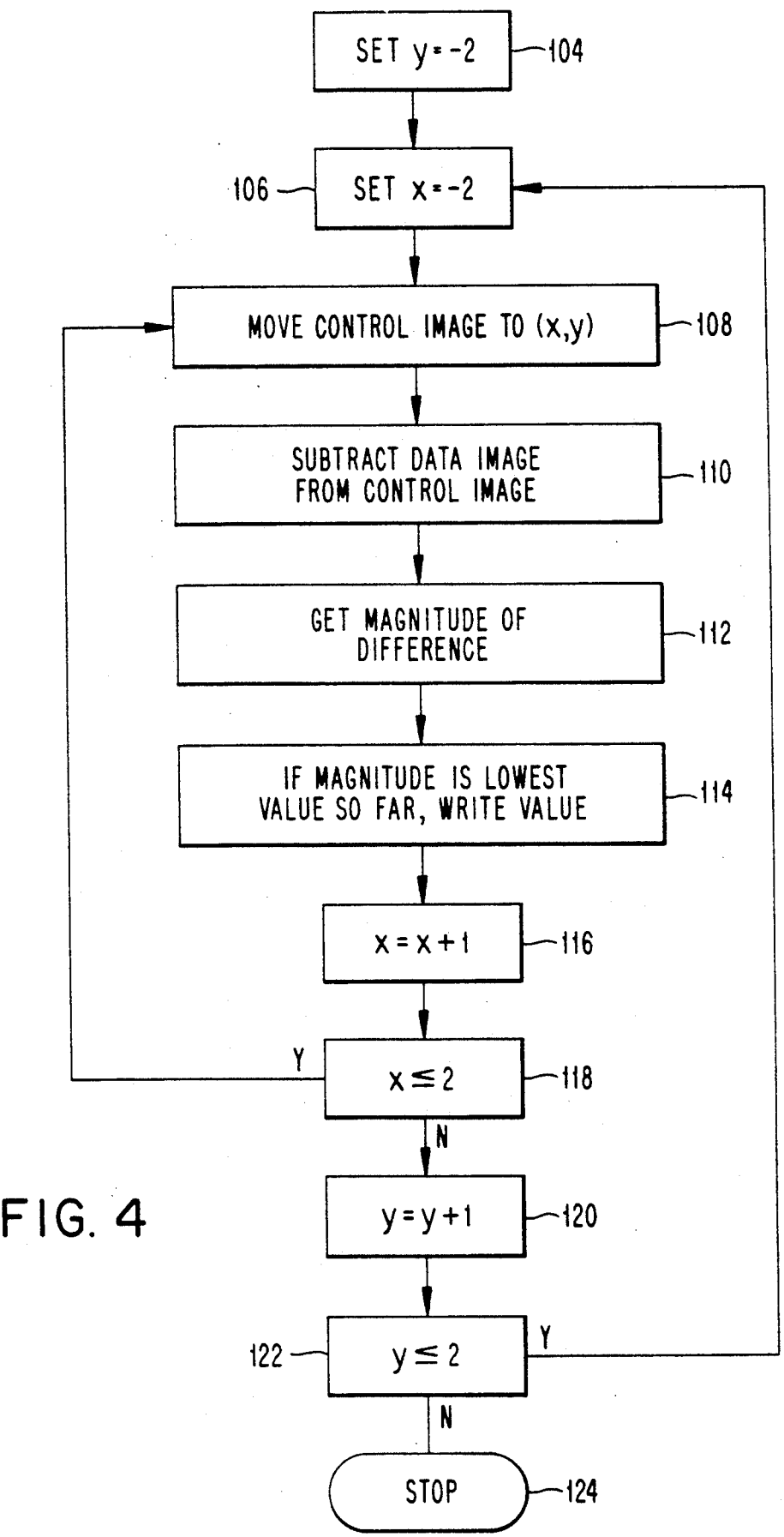
FIG. 4 is a flow chart illustrating an exemplary method for implementing an automated spatial warping of two image frames.
Figure 5:
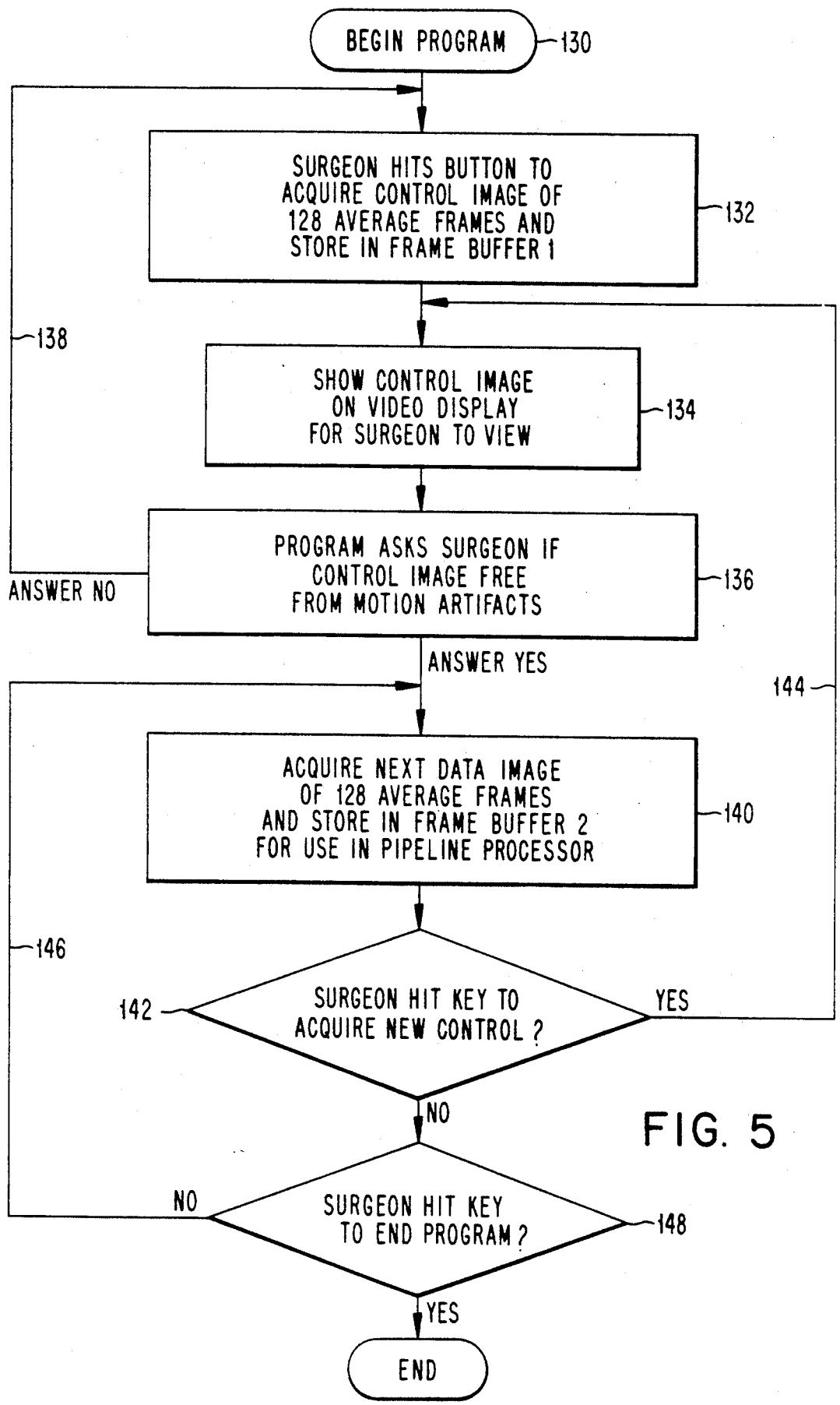
FIG. 5 is a flow chart illustrating imaged results obtained using the inventive method and apparatus; and, FIGS. 6A-G are a series of composite images produced and displayed during in vivo analysis of a human cortex in accordance with an exemplary embodiment of the present invention.
Figure 6A:
Figure 6B:
Figure 6C:
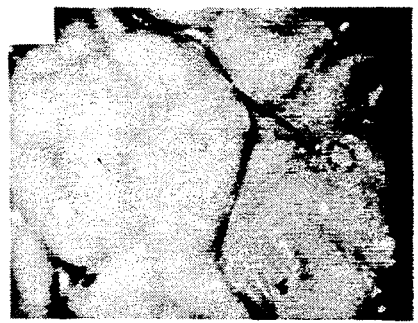
Figure 6D:
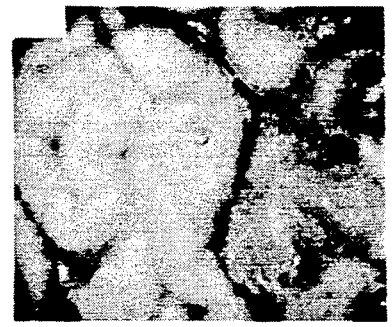
Figure 6E:
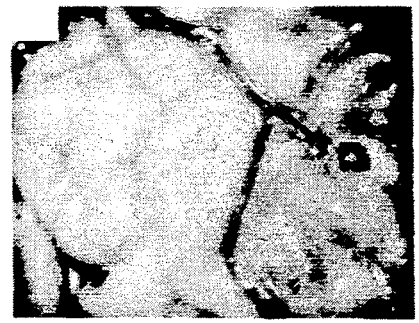
Figure 6F:
Figure 6G:
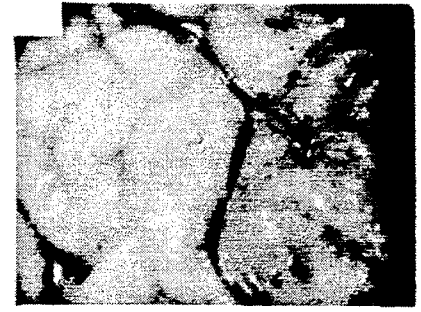

However, in a more preferred embodiment to be described in conjunction with the flow charts of FIGS. 3 to 5, a speed enhanced pipeline version of the present inventive method will be presented, wherein live, on-line analysis of averaged images permits real time viewing of displayed results in an operating room. In this embodiment, use of a real time processor as described previously can be used to further enhance processing speed.

Figure 2:
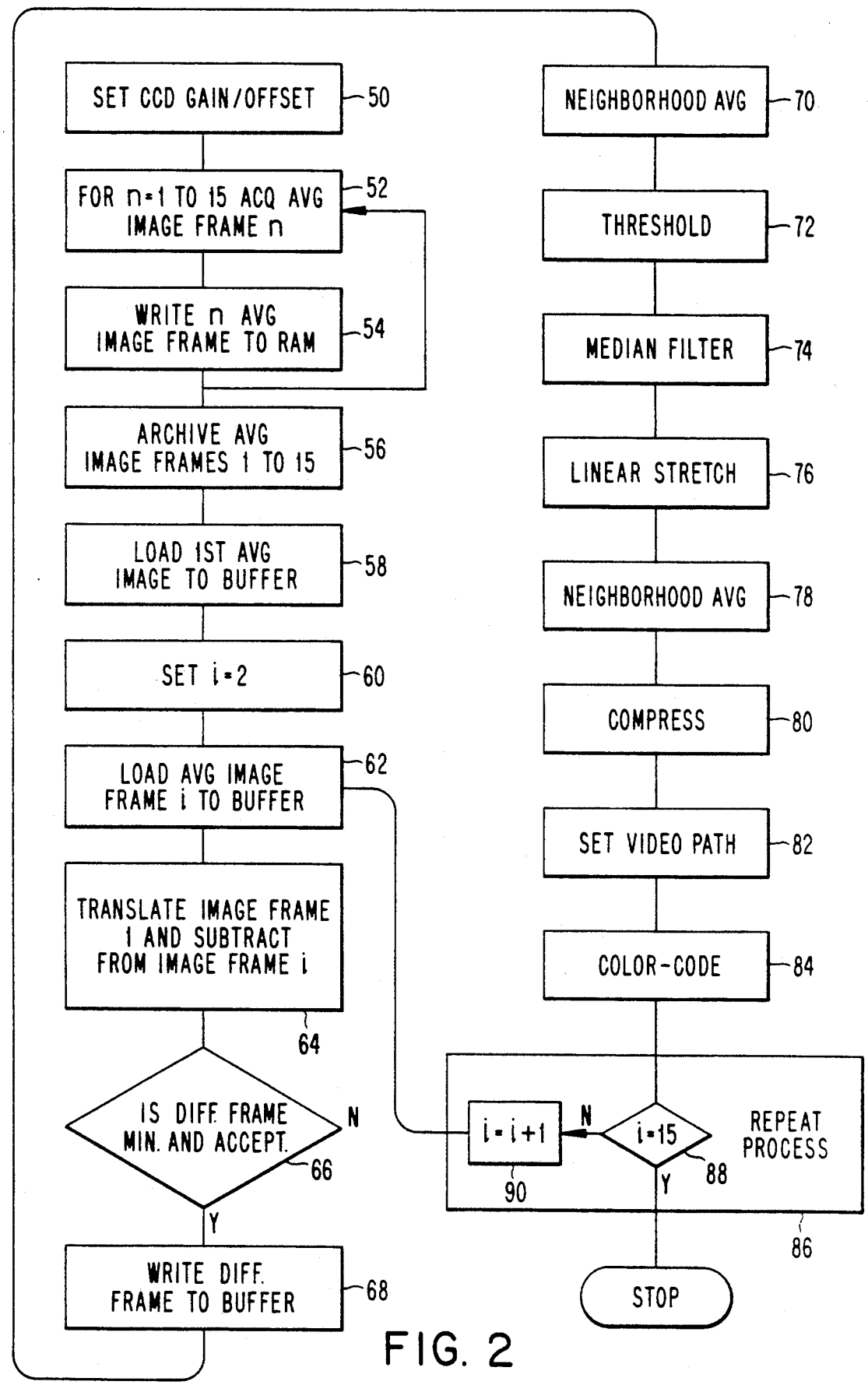
FIG. 2 is a flow chart illustrating an exemplary method for implementing the present invention in a post data acquisition analysis mode.

As shown in FIG. 2, a first step 50 of an image acquisition and storage operation which provides post acquisition analysis of image data involves setting the gain and offset on the CCD video camera 10. The gain and offset of the CCD video camera are adjusted so that the image intensity spans the full dynamic range of the A/D interface 16 without saturating minimum or maximum input levels of the A/D interface.

Once the gain and offset of the CCD video camera have been properly adjusted, a series of averaged images from the cortical area being observed are obtained in step 52. In an exemplary embodiment, 15 frames of averaged images are obtained, each of these frames corresponding to an average of 128 frames of digitized video signals corresponding to digitized image data received by the image analyzer 12. Each averaged image frame can be obtained by adding 128 frames as they are received by a 16-bit frame buffer area (e.g., frame buffer area 21) and then dividing each pixel by 128. Each averaged image frame is thus obtained by pipelining the analog video signal from the CCD video camera through the A/D interface, the ALU 20 and the frame buffer 18 of the image analyzer 12.

In the exemplary embodiment to be described with respect to FIG. 2, the first three averaged image frames are digitized control images used to monitor the stability of the received analog video signal. As referenced herein, a control image is an image of the cortical area which is obtained during a control period, the control period being characterized by a substantial absence of stimuli to the cortical area being observed. A substantial absence is achieved by refraining from application of external stimuli (e.g., electrodes placed around or near an external area of the patient to be stimulated, such as a finger) or evoked seizures (e.g., application of medication likely to stimulate a seizure, such as an epileptic seizure) and by requesting, for example, an awake patient to remain still during the control period.

The fourth through sixth frames of averaged images are obtained during three stimulation periods. During a stimulation period, the same or different stimuli (e.g., ring electrodes, evoked seizures) are applied to generate neuronal activity in the cortex. During each of the three stimulation periods, 128 frames of analog image data from the CCD video camera are obtained, averaged and stored as described previously. The seventh through fifteenth frames of averaged images obtained reflect the recovery of the cortical area being observed after the stimuli has been removed.

After a given one of the fifteen averaged images has been stored in the frame buffer 18, it is subsequently written to a random access memory in the computer 8, as indicated by step 54 in the FIG. 2 flow chart. Steps 52 and 54 are repeated for each of the fifteen averaged images. A permanent archive of all images obtained is then updated in step 56 by copying the fifteen most recent images to the optical disk 34 of FIG. 1 from the RAM in computer 8. The write of each averaged image frame to RAM is performed first because the time required to store the fifteen frames of averaged images in RAM (e.g., 1 sec) is considerably less than the time required to write the fifteen frames of averaged images to the optical disk. It will be appreciated that if a frame buffer of sufficient size is provided, the 15 averaged image frames could be stored therein without archival transfer to the optical disk via the computer RAM.

Having completed the acquisition of the fifteen frames of averaged images, a post acquisition analysis of the data can be performed as follows. Beginning with step 58 in the FIG. 2 flow chart, the frame storage area 17 in the frame buffer 18 is loaded with the first averaged image frame corresponding to the first control image, from either the RAM of computer 8 or from the optical disk 34. The second averaged image frame is subsequently loaded into the frame storage area 19 of frame buffer 18 from the RAM or the optical disk during steps 60 and 62. In step 64 of the FIG. 2 flow chart, the first averaged image frame (corresponding to the first control image) presently stored in the frame storage area 17 is subtracted in real time, pixel by pixel, from the second averaged image (corresponding to the second control image) stored in the frame storage area 19. This subtraction yields a difference frame of image data which is, for example, stored in the frame storage area 21.

Each pixel in the difference frame possesses an intensity value represented by 8-bits which corresponds to the intensity difference between a single pixel intensity in each of the two averaged image frames being compared. Accordingly, if the first and second averaged image frames correspond to control images generated during control periods when substantially no input stimuli to the cortical area was present, then ideally a subtraction of these two frames would yield a difference frame wherein all pixel values are zero. However, because the surgeon cannot prevent all involuntary stimuli of the patient, some difference frame pixels will reflect minor changes in cortical activity. Further, some noise will likely be present in the difference frame due, for example, to glare which impacts the video camera differently over time as a result of patient movement, cortex swelling, etc.

In addition, patient movement, cortex swelling, respiratory movement, etc. can result in misalignment of the first and second averaged image frames. In this case, most of the pixel values in the difference frame are likely to possess detectable intensity values. However, such misalignment of the two averaged image frames being compared can be corrected by geometrically transforming or spatially translating the position or orientation of one averaged image frame relative to the other and reexecuting the subtraction. These steps can be repeated until the net intensity values of all pixels in the difference frame is minimized to provide a baseline indication of background noise present.

For this purpose, decision step 66 provides for a visual determination by the surgeon as to whether the difference frame is considered minimal and acceptable. A difference frame is considered acceptable if a sufficient number of pixels in the difference frame of image data formed by subtracting each of the corresponding pixels in the two averaged image frames does not result in a frame of data composed of pixel values above a predetermined threshold (e.g., all pixels have a value greater than roughly 50 percent of their potential maximum value, 255). The surgeon would readily notice that the difference frame produces an image on the monitor having a number of brightly illuminated pixels in this case. Similarly, motion artifacts can be detected by identifying brightly illuminated areas of the difference frame image corresponding to portions of the image which could not possibly or which are highly unlikely to produce intrinsic signal changes (e.g., vasculature).

A difference frame is considered minimal if the frame of pixels used to form the first control image cannot be spatially translated (i.e., warped) by shifting the entire frame one column of pixels to the right or left, or one row of pixels up or down to further reduce the net sum of all pixel values forming the difference frame. The surgeon would readily notice that the difference frame produces almost an entirely dark image when the two averaged control image frames are properly aligned.

Once an acceptable and minimal difference frame is obtained, the pixel values associated with the difference frame are written into the frame storage area 21 of frame buffer 18 in step 68. In step 70, a neighborhood average is carried out by using the ALU 18 and to execute a convolution of the difference frame with a 5 pixel by 5 pixel pill box kernal. More specifically, for each pixel of the difference frame, a resultant value is assigned on the basis of the neighboring pixel values surrounding the pixel. In determining the resultant value to be assigned the center pixel(s) of the 5 by 5 pixel "pill box", all of the surrounding pixels in the 5 by 5 pill box (excluding the center pixel(s)) are multiplied by kernal constants in known fashion, summed and scaled. The resulting value is then assigned to the center pixel(s). In an exemplary embodiment, the kernal is chosen to provide equal weight to all surrounding pixels so that an average intensity (rounded off to an 8-bit integer) of the pill box area will be assigned as the resultant value.

Following a neighborhood averaging of all pixels in the difference frame, all of the resultant pixel values are compared with threshold values to further reduce noise due, for example to glare or involuntary movement by the patient. Accordingly, in step 72 all resultant pixel values less than or equal to 1 are considered to be indicative of pixels where the subtracted images canceled and should therefore be set to a value of zero.

Further, all resultant pixel values greater than or equal to 5 are considered to be indicative of pixels where noise was present in one of the two images subtractively combined, and similarly are set to a value of zero. The thresholding can, for example, be performed using the programmable look-up table 25 of the ALU. More specifically, a linear function is assigned to the look-up table so that when a pixel value less than or equal to one, or greater than or equal to 5 is input, a value of zero is output. All resultant pixel values corresponding to integers between 1 and 5 retain their original value.

In step 74, the ALU 20 performs a median filter of the difference frame output from the threshold look-up table. For example, for each pixel of the difference frame, a 3 by 3 pixel kernal is used to identify those pixels immediately surrounding a pixel of interest. The values are then sorted lowest to highest, with the value of the median pixel being selected and assigned to the center pixel of interest. All other pixels identified by the kernal retain their original value. The kernal is subsequently moved about the entire difference frame, and the process repeated for each pixel.

In step 76, a known linear stretch of the median filtered difference as described for example in "Digital Image Processing- A Systems Approach", Green, William B., New York: Van Nostrand Reinhold, 1989 (see also "Digital Image Processing", Gonzalez, R. and P. Wintz, New York: Addison-Wesley, 1977), is performed. In accordance with an exemplary embodiment of the present invention, the linear stretch is performed by setting a pixel value of 1 to 0 and by setting a pixel value of 5 to 255 (since the 8-bit representation of each pixel can provide a resolution of up to 256 values). All pixel values between 1 and 5 are then linearly mapped with a value of 0 to 255.

In linearly mapping the pixel values over a larger range, relative differences between grey values of the pixels are retained. Stretching the image permits easier identification of noise and causes levels of magnitude of intrinsic signals to be better distinguished. Further, by linearly stretching the image prior to subsequent filtering (e.g., neighborhood averaging), intrinsic signal information included in the difference frame image is less likely to be lost due to spatial averaging.

Another neighborhood averaging of the linearly stretched difference frame is performed in step 78 using a 5 by 5 pixel kernal as described previously with respect to step 70. As with step 70, the ALU 20 can be utilized in known fashion to execute the convolution associated with this step.

A compression of the values used to represent pixel intensities in the difference frame is subsequently performed in step 80. For this purpose, the programmable look-up table of the ALU in the image analyzer 12 is programmed so that for pixel values from 0 through 255:

a value of 0 is set to a value greater than 3 (e.g., 255),
values of 1 through 64 are set to a set value 0,
values of 65 through 128 are set to a set value 1,
values of 129 through 192 are set to a set value 2,
values of 193 through 255 are set to a set value of 3.

As a result of the foregoing analysis, a compressed difference frame will be provided, and will produce an image highlighting cortical areas of neuronal activity.

Although compression of the difference frame image may reduce contrast within the image, it simplifies graphical overlay of the difference frame image onto another image presently appearing on the monitor 38 and/or 40 (e.g., an averaged image which has not been subtracted from another image) when using the Series 151 image processor. In an exemplary embodiment the color of any pixel on the output screen of monitor 38 or 40 can be determined by a mix of red, green and blue using look-up tables associated with the A/D interface. Alternately, a difference image output could consist of pixels represented by different intensities of the same color or a grey code output could be used.

In accordance with an exemplary embodiment, each of the set values 0, 1, 2 and 3 identify one of 4 banks of look-up tables included with the Series 151 ADI-150 module. Each of these banks of look-up tables includes 3 look-up tables: one for red, one for green, and one for blue. For example, the pixel values 1 through 64 are assigned the red, green and blue values established in a first bank of look-up tables identified by the set value 0.

Representative intensity values for red, green and blue values associated with each of the four banks of look-up tables 0 to 3 can be as follows:

| Set value | 0 | 1 | 2 | 3 |
|---|---|---|---|---|
| Red | 0 | 150 | 255 | 255 |
| Green | 255 | 150 | 100 | 0 |
| Blue | 0 | 0 | 0 | 0 |

These values have the effect of making low values of the intrinsic signals appear bright green, middle-low values yellow, middle-high values orange, and high values bright red. However, it will be appreciated that the color-code settings can be modified as desired during an initialization period before execution of the FIG. 2 flow chart. In order for the background of the difference frame image to remain transparent so it may be overlaid upon an image of the cortical area being observed, a pixel intensity value of zero is assigned a set value for which no bank of color-coding look-up tables exist on the A/D interface (e.g., any number greater than 3, and preferably 16 for use with the Series 151 image processor which has look-up tables 0–15).

In step 82, the surgeon establishes a video path between the second frame storage area 19 and a video monitor (i.e., monitor 38 and/or 40). The second averaged image frame is then reloaded into the frame storage area 19 by transferring the pixel values corresponding to the second averaged image from the RAM of the computer or the optical disk 34. Placement of the second averaged image frame into the frame storage area 19 enables this image to be reproduced on either or both of the monitors 38 and 40 in FIG. 1. Although overlay on the second averaged image is described herein, it will be apparent to those skilled in the art that overlay on any image (e.g., the first averaged image) could be executed via appropriate routing of a video path to the monitor(s).

The compressed difference frame image can then be superimposed on the averaged control image to clearly identify those portions of the control image currently undergoing neuronal activity. For this purpose, the look-up table of the ALU 20 is set to a dynamic mode for the compressed difference frame image whereby the aforementioned look-up tables associated with the A/D interface can be accessed. The look-up tables included with the A/D interface are initialized at the start of the analysis to provide a predetermined color code which is coordinated to the values of a compressed difference image.

Accordingly, after the digitally enhanced difference frame image has been produced, each of the pixels included in this frame is assigned a color based on its value of 0 through 3 using the A/D interface look-up tables. As a result, a color-coded compressed difference frame image is superimposed on the averaged control image currently being displayed on the monitors 38 and 40.

It will be appreciated that when two control images are subtracted to provide the aforedescribed difference frame, ideally no color-coded image will result for superimposition upon the averaged image frame. However, if a control image is subtracted from an averaged image frame generated during or subsequent to a stimulation period, a color-coded compressed difference frame image should result. In this case, superimposition of the color-coded compressed difference frame image on the averaged image frame from which the control image was subtracted will identify those portions of the observed cortical area undergoing functional cortical activity as a result of the stimuli. Accordingly, the foregoing steps are repeated for each of the third through fifteenth averaged images as indicated by step 86, wherein the number of the averaged image frame being compared with the first control image is incremented via substeps 88 and 90 until the last (i.e., fourteenth) color-coded difference frame image has been generated and superimposed on the fifteenth averaged image frame stored in the RAM and/or optical disk After completion of the fourteenth superimposition, a new set of fifteen averaged images could again be generated and the foregoing process repeated. Alternately, any or all of the foregoing images could be again recalled from videotape or optical disk and either displayed once more or printed out.

FIG. 6 shows exemplary results obtained using the inventive method and apparatus. As can be seen in FIG. 6, image A corresponds to an averaged image frame which has been stored in the second frame storage area 19 at the start of a stimulation period. Each of images B, C and D in FIG. 6 represent the updated superimposed images obtained on the monitor 40 during each of three stimulation periods (using the same stimulus) when a color-coded difference frame image is, laid over the current averaged image frame stored in the second frame storage area 19. Each of images E, F and G in FIG. 6 correspond to superimposed images obtained on the monitor 40 following the stimulation periods (i.e., post stimulation). For this reason, the overlaid, color-coded difference frame image can be seen to gradually diminish.

Thus, using the composite images of FIG. 6, the surgeon could identify those portions of the cortical area where neuronal activity associated with, for example, an epileptic seizure foci is located. Removal of the brain tissue beneath the color-coded difference frame image can then subsequently be performed.

Using present EEG techniques, a surgeon is likely to remove a significant portion of the cortical area shown in the analog video signal of FIG. 6 to ensure removal of the tissue possessing the epileptic foci. However, the higher resolution provided by the present invention will often permit a substantial reduction in the amount of brain tissue which must be removed to ensure treatment of a neurological defect such as intractable epilepsy. Further, the enhanced resolution of the present invention permits much more accurate removal of, for example, tumors and avoids to a much greater extent the removal of critical cortical areas unaffected by the tumor.

It will be apparent to those skilled in the art that more or less than fifteen averaged images could be used in accordance with the present invention. Further, more or less than 128 frames of image data could be used to generate each of the averaged image frames. For example, a single frame of image data could be used in which case averaging of each image frame would not be necessary. While the number of frames of image data used to generate an averaged image can be increased, such an increase would affect the speed of the foregoing data acquisition and possibly require use of a more powerful (e.g., faster) computer and/or image analyzer. Similarly, the values chosen for the neighborhood averaging, thresholding, median filtering, linear stretching and compressing steps described above are considered to be merely exemplary values and in no way is the present invention to be construed as being limited to these values.

For example, it would be apparent to one skilled in the art that if a greater number of bits were used to represent the intensity of each pixel in an averaged digital image, a greater linear stretch could be provided. Also, if a large range of pixel intensity values exist in a difference frame image to be stretched (e.g., a range of greater than 5 possible integer values is permitted), a linear histogram stretch may be implemented to increase contrast of the image.

As referenced herein, a linear histogram stretch is used to stretch a small region of the difference frame image where most pixel intensities fall. Although the threshold step 72 is intended to reduce the range of pixel intensities stretched, use of a linear (or non-linear) histogram stretch can be invoked to further enhance the difference frame image and could be implemented using the means 13 for establishing a histogram in conjunction with a look-up table. Similarly, the threshold cut-off values established in the programmable look-up table of the ALU could be modified to increase or decrease the range of pixel values which would be set to zero. Further, a larger or smaller kernal could be used in the neighborhood averaging and a larger or smaller median filter could be chosen (e.g., a 9 by 9 window could be used).

In addition, the present invention is not to be construed as limited to the use of a 512 by 512 digital image. For example, a digital image of lesser or higher resolution (e.g. 1024 by 1024 pixel array) could equally be used With the present invention. A digital image of higher resolution can be used either with a comparably sized monitor screen or with a smaller monitor screen using, for example, a slow scan or a scroll viewing technique.

Further, it would be apparent to one skilled in the art that a greater or lesser number of control frames could be used to verify a non-stimulated or stimulated condition of the cortical area under investigation. For example, if there is reasonable assurance that a non-stimulated condition of the cortical area under examination exists, the second averaged image could correspond to an image obtained during a period of stimulation. Alternately, control periods could be initiated with a greater frequency than that described above. For example, a control period could be initiated to generate a control image in every other averaged image frame.

In accordance with a second preferred embodiment of the present invention, an enhanced, automated pipeline version of the aforedescribed image analysis is provided, wherein live analysis of averaged images is available to a surgeon in the operating room. This version will be described with respect to the flow chart of FIG. 3.

Before describing the FIG. 3 flow chart, it should be pointed out that, as mentioned previously, slight modifications to the FIG. 1 system are preferred for executing on-line analysis in connection with the present invention. For example, where the aforementioned Series 151 image processor is used as the image analyzer 12, a 12 slot IEEE standard VME bus as opposed to a 7 slot VME bus is preferred to, for example, accommodate use of the real time modular processor. Because a real time modular processor is unnecessary for the post acquisition analysis described with respect to the FIG. 2 flow chart, a 7 slot VME bus is generally adequate for the aforedescribed exemplary embodiment where the Imaging Technology Inc. Series 151 image processor is used.

An on-line image processor for permitting live analysis of averaged images also includes the A/D interface 16, the frame buffer 20, the ALU 18, and a histogram establishing means such as the known "Histogram/Feature Extractor HF 151-1-V" having a single, dedicated buffer. Further, the on-line system preferably includes use of the aforementioned real time modular processor, such as the Imaging Technology Inc. RTMP described previously. For example, three of the "RTMP 151-V" Imaging Technology Inc. real time modular processors are preferably used: one with the aforementioned real time sobel computation module such as the Imaging Technology Inc. "CM 151-RTS" and a look-up table such as the Imaging Technology Inc. "CM 151 LUT16"; one with a rank value filter such as the Imaging Technology Inc. "CM 151-RVF8" and a real time sobel computation module such as the Imaging Technology Inc. "CM 151-RTS"; and one with two look-up tables such as the Imaging Technology Inc. "CM 151-LUT16" modules.

Operation of an on-line averaged image analysis system using a real time processor will now be discussed. As can be seen in step 100 of the FIG. 3 flow chart, a first averaged control image frame and a second averaged image frame to be subtracted from the control image frame are placed into first and second frame storage areas 17 and 19, respectively of the frame buffer 20 in a manner similar to that described with respect to FIG. 2. In step 102, a warp and subtraction of the two averaged images presently stored in the first and second frame storage areas 17 and 19 is executed using the histogram establishing means 13.

More specifically, in order to best highlight respective pixel intensity differences between the two averaged image frames being subtracted from one another, it is important that the two images associated with these frames be matched with one another to the greatest extent possible. As referenced herein, the two images are best matched when a pixel in a first averaged image frame used to store information regarding a portion of the cortical area being observed is subtracted from the pixel in the other averaged image frame which also has stored information from that same portion of the cortical area being observed. As a result, pixel intensities of the two images being compared which correspond to observed areas of the cortex where no changes in neuronal activity have occurred will cancel one another. A resultant difference frame will therefore be produced wherein pixel values will have intensities corresponding to the intensity changes for a given portion of the observed cortical area where neuronal activity has occurred.

A flow chart of an automated warping technique for geometrical transformation is illustrated in FIG. 4, wherein it is initially assumed that the averaged control image frame in the first frame buffer area is located at coordinates (0,0). As can be seen therein, an x and a y value are then preset to −2 at steps 104 and 106, and the averaged control image moved (i.e., warped) to this location in step 108. In steps 110 to 114, the warped averaged control image frame and the second averaged image frame are subtracted from one another pixel by pixel, with all resultant difference pixel values being summed and compared with the lowest previously stored net resultant value (NB.: for the first subtraction, the net resultant value is stored regardless of its value to establish an initial threshold). The foregoing steps are repeated for values of x up to and including 2, with the value of y remaining −2. Once the value of x has reached 2, then the steps are repeated for different y values up to and including 2, with the y value being incremented until it also reaches a value of 2 as indicated by steps 116 to 124. A resultant difference frame is thus provided as a result of the warp and subtraction step 102 in FIG. 3.

It will be appreciated by those skilled in the art that the foregoing warping technique is one of many which could be implemented in accordance with the present invention. The FIG. 4 technique is therefore considered to be merely illustrative of but one exemplary technique which could be implemented in accordance with the present invention. For example, a warping technique could also be implemented by choosing larger initial or larger cutoff values for the x and/or y values, or by obtaining a magnitude of difference between a warped averaged image frame and a second averaged image frame for all values of x and y selected. Further, warping techniques can be implemented which rotate one image frame relative to another by shifting all pixels of one image frame diagonally within a frame buffer. These warping techniques include, but are not limited to techniques commonly referred to as "rubber sheet transformations", which provide warping due to motions in three-dimensional space.

Returning to FIG. 3, a neighborhood averaging of the resultant difference frame is performed in step 104 using, for example, a 5 by 5 pixel pill box as described previously in connection with the FIG. 2 flow chart. However, to enhance the speed with which the neighborhood averaging is performed, use of the aforementioned real time sobel and convolution module 26 in the real time processor 24 is preferred.

In step 106, pixel values of the neighborhood averaged difference frame are subjected to thresholds in a manner similar to that described above in step 72 of the FIG. 2 flow chart. Again, to enhance processing speed when using the exemplary Series 151 image processor as the image analyzer 12, the thresholding of the FIG. 3 flow chart is preferably implemented using the look-up table module 28 of the real time processor.

Median filtering of the difference frame, as described previously with respect to step 74 of FIG. 2, is executed in step 108 of the FIG. 3 flow chart. However, to enhance processing speed when using a Series 151 image processor, use of the aforementioned rank value filter 30 with the real time processor 24 is preferred.

A linear stretch of the filtered difference frame is performed in step 110. This step basically corresponds to that of step 76 in the FIG. 3 flow chart except that it is preferably performed on-line using the look-up table 37 included with the real time processor.

The second real time sobel and convolution module 31 included with the real time processor 24 as described previously is used to execute a second neighborhood averaging of the linearly stretched difference frame in step 112. In step 114, the linearly stretched difference frame is compressed in a manner similar to that previously described with respect to step 80 in the FIG. 2 flow chart to provide a compressed difference frame image. However, because a real time modular processor is preferably included in the system used to execute the FIG. 3 flow chart, the look-up table 39 of the real time processor 24 is preferably used to enhance processing speed.

A previously initialized A/D interface is used in step 116 to permit superimposition of the compressed difference frame image on an averaged image frame previously stored in the second frame buffer area to provide a composite image, as described with respect to steps 82 and 84 in the FIG. 3 flow chart. In step 118, the composite image is stored and archived on videotape using, for example, the FIG. 1 VCR 42.

Thus, using the FIG. 1 system with the real time processor 24 permits an on-line, live analysis of an observed cortical area in accordance with the exemplary flow chart of FIG. 3. Accordingly, a surgeon could use the inventive system and method to examine a patient's cortex during neurosurgery and to perform brain tissue removal using the displayed composite image which is updated on a real time basis.

Again, as with the exemplary FIG. 3 post-acquisition mode, parameters selected for the various steps of the exemplary FIG. 4 on-line analysis mode can be modified without departing from the spirit of the invention. For example, as described previously, features such as the number or frequency of control images, the number of data frames averaged to form an averaged data frame, or the kernal size selected for any of the neighborhood averaging steps can be modified as desired. Further, image frames using a greater number of pixels to represent an image and/or difference image can be used.

Also, in any of the aforedescribed exemplary embodiments, different methods of illuminating the brain can be used. For example, a ring shaped light source can be used to more uniformly illuminate the exposed cortex. Alternately, an operating room light of sufficient intensity may be adequate to permit intrinsic signal detection.

FIG. 5 shows an exemplary flow chart for use by a surgeon to assist in the identification of brain tissue in an observed cortical area during neurosurgery. The FIG. 5 flow chart would therefore be executed by the computer 8 in response to keyboard inputs by the surgeon, and would be used in conjunction with the FIG. 3 flow chart to permit on-line analysis of a cortical area.

In accordance with the FIG. 5 flow chart, the surgeon begins with step 130 by activating the on-line analysis represented by the FIG. 3 flow chart using, for example, a start button on the keyboard 9 in FIG. 1. In step 132, the surgeon activates a key on the keyboard to acquire an averaged control image represented by the aforementioned averaging of 128 frames of digitized image data. The averaged control image is then stored in a first frame storage area of the frame buffer 20 as described previously.

In step 134, the averaged control image is displayed on, for example, the monitor 40 of FIG. 1 for the surgeon to view. In step 136, the FIG. 5 interface program subsequently displays a request to the surgeon viewing the averaged control image as to whether the image is substantially free from motion artifacts. The surgeon will respond affirmatively (e.g., key in an answer yes) if the averaged control image appearing on the monitor appears visually clear (i.e., free of apparent visual blur). However, if the displayed averaged control image does not appear visually clear to the surgeon, a no would be keyed in by the surgeon after which the FIG. 5 interface flow chart would prompt the surgeon to key in a new request for acquisition of an averaged control image via flow chart path 138.

If the acquired, averaged control image was deemed satisfactory to the surgeon, step 140 of the FIG. 5 flow chart prompts the surgeon to key in a request for another averaged image, which may either be another control image for comparison with the first averaged control image, or which may be an averaged image obtained during or immediately after a stimulation period as described with respect to the FIG. 2 and FIG. 3 flow charts. Upon entry of the request in step 140, the pipeline processing described with respect to the FIG. 3 flow chart would be executed to produce a composite image for viewing by the surgeon on the monitor 40.

In step 142 of the FIG. 5 flow chart, the surgeon is prompted to request a new averaged control image in the first area of the frame buffer. If the surgeon responds affirmatively, the FIG. 5 flow chart reexecutes the foregoing steps, beginning with step 134, as represented by line 144. Alternately, if the surgeon responds negatively, the FIG. 5 flow chart returns to step 140, as represented by the line 146. Step 140 can thus be repeated for any number of averaged image frames which the surgeon wishes to compare with the first averaged control image stored in the first frame storage area of the frame buffer 20, assuming a key to end execution of the FIG. 5 flow chart was not activated in step 148. Step 140 will thus be automatically repeated unless a program ending interrupt key is executed in step 148.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. Method for optically imaging neuronal activity of in vivo mammalian cortical areas comprising the steps of:
   illuminating an in vivo cortical area of a mammalian brain with a regulated light source;
   focusing a magnification lens on said cortical area;
   detecting light reflected from said cortical area along a path through said magnification lens as an analog video signal representative of intrinsic signals, said intrinsic signals being generated in response to intrinsic characteristics of said cortical area;
   digitizing said detected analog video signal to provide at least one frame of digitized image data;
   acquiring and analyzing a plurality of frames of said digitized image data to identify changes in said intrinsic signals, said step of acquiring and analyzing further including the steps of:
   averaging a series of frames of said digital image data during a control period to provide a first averaged image frame, said control period being characterized by a substantial absence of input stimuli to the brain;
   storing said first averaged image frame;
   applying a predetermined input stimuli to the brain during a stimulation period;
   averaging a second series of frames of said digitized image data during said stimulation period to provide a second averaged image frame;
   storing said second averaged image frame;
   subtractively combining said first averaged image frame with said second averaged image frame to provide a first difference frame, said step of subtractively combining further including a step of spatially translating said first averaged image frame relative to said second averaged image frame;
   filtering said first difference frame to reduce noise;
   enhancing said first difference frame using a linear look-up table to stretch pixel values composing said difference frame;
   filtering said stretched difference frame;
   compressing and color-coding said difference frame; and,
   superimposing an image of said color-coded difference frame upon a video image of said first or second averaged image frame to provide a composite image for identifying those portions of said cortical area subject to neuronal activity in response to said predetermined input stimuli.

2. Method according to claim 1, wherein said step of acquiring and analyzing further includes the steps of:
repeating said steps of averaging and storing to acquire at least one additional averaged image frame during said control period; and,
subtractively combining said first averaged image frame and said at least one additional averaged image frame to confirm a substantial absence of input stimuli during the control period.

3. Method according to claim 1, wherein said step of acquiring and analyzing further includes the steps of:
applying at least one additional predetermined input stimuli to the brain during at least one additional stimulation period to acquire at least one additional stimulated averaged image frame;
repeating said steps of subtractively combining, enhancing, filtering, compressing and superimposing for each of said additional stimulated averaged image frames to provide an updated composite image.

4. Method according to claim 1, wherein said step of superimposing further includes a step of comparing each pixel value used to compose said difference frame with at least one threshold value to provide an enhanced color-coded difference frame.

5. Method according to claim 1, wherein said mammalian brain is an in vivo, human brain.

6. Method for optically imaging neuronal activity during neurosurgery comprising the steps of:
illuminating a cortical area;
detecting light reflected from said cortical area; and
acquiring and analyzing a digitized image obtained from said detected light during neurosurgery to provide on-line identification of those portions of said cortical area where neuronal activity has occurred, wherein said step of acquiring and analyzing further includes a step of obtaining said digitized image by subtractively combining at least two image frames of data obtained from said reflected light, said two image frames being spatially translated relative to one another.

7. Method according to claim 6, wherein said step of acquiring and analyzing further includes the steps of:
displaying an analog video image of said cortical area; and
superimposing said digitized image on said analog video image of said cortical area to provide a composite image which identifies said cortical area portions where neuronal activity has occurred.

8. Method according to claim 7, wherein said step of acquiring and analyzing further includes the step of updating said composite image in real time during said neurosurgery.

9. Method according to claim 8, wherein said step of updating occurs at a rate of at least 1/30th of a second.

10. Method for optically imaging cortical activity of a mammalian brain comprising the steps of:
detecting light reflected from a cortical area;
storing at least two frames of data obtained from said reflected light;
analyzing said at least two frames to identify intrinsic signal changes of said cortical area, said step of analyzing further including the steps of:
spatially translating said at least two frames relative to one another; and,
subtractively combining said at least two frames to provide a difference frame.

11. Method according to claim 10, wherein said difference frame is composed of an array of data elements representative of reflective light intensity differences in said cortical area and said step of analyzing further includes the steps of:
identifying an acceptable range of intensity differences; and,
stretching intensity differences in said acceptable range over a larger range of values.

12. Method according to claim 11, wherein said step of stretching includes linearly stretching said intensity differences in said acceptable range to retain relative differences between said intensity differences.

13. Method according to claim 12, wherein said step of analyzing further includes the steps of:
assigning an intensity value to each data element in said array based on an average of intensities associated with data elements in a predetermined proximity to each data element; and,
subsequently assigning an intensity value to each data element in said array based on a median value associated with data elements in a predetermined proximity to each data element.

14. Method according to claim 13, wherein said steps of assigning are performed prior to said step of stretching.

15. Method according to claim 13, wherein said step of analyzing further includes the steps of:
compressing a range of intensity values used to represent said data elements; and,
color-coding said data elements based on said compressed range of intensity values.

16. Method according to claim 10, wherein said difference frame is composed of an array of data elements representative of reflective light intensity differences in said cortical area, and wherein said step of analyzing further includes the steps of:
color-coding said difference frame based on said intensity values; and,
superimposing said color-coded difference frame upon an image corresponding to one of said at least two frames.

17. Method according to claim 10, wherein said steps of storing and analyzing are dynamically performed in real time.

18. Method according to claim 17, wherein said mammalian brain is an in vivo, human brain.

19. Method according to claim 10, wherein each of said at least two frames is composed of averaged data from a plurality of frames of said detected light.

20. Method according to claim 10, wherein at least one of said at least two frames is obtained during a control period characterized by a substantial absence of external stimuli to the cortical area.

21. Method according to claim 20, wherein at least another of said at least two frames is obtained during a stimulation period characterized by the presence of a stimulus to the cortical area.

22. Method according to claim 21, wherein said stimulus is a medication.

23. Method according to claim 21, wherein said stimulus is applied to a non-cortical part of a patient to evoke a reaction in said cortical area.

24. Method according to claim 20, wherein at least another of said at least two frames is obtained during a post-stimulation period characterized by a recovery of the cortical area to a discontinued stimulus.

25. Apparatus for optically imagining neuronal activity of in vivo mammalian cortical areas comprising:
   a regulated light source for illuminating an in vivo cortical area of a mammalian brain;
   a magnification lens for focusing said light source on said cortical area;
   a filter for filtering light reflected from said cortical area along a path through said magnification lens;
   means for detecting said filtered light as an analog video signal representative of intrinsic signals, said intrinsic signals being generated in response to intrinsic characteristics of said cortical area;
   means for digitizing said detecting analog video signal to provide at least one frame of digitized image data;
   means for acquiring and analyzing a plurality of frames of said digitized image data to identify changes in said intrinsic signals, said acquiring and analyzing means further including:
      means for averaging a series of frames of said digital image data during a control period to provide a first averaged image frame, said control period being characterized by a substantial absence of input stimuli to the brain, said averaging means averaging a second series of frames of said digitized image data during a first stimulation period to provide a second averaged image frame and for spatially translating said first averaged image frame and said second averaged image frame relative to one another;
      means for storing said first averaged image frame and said second averaged image frame;
      means for subtractively combining said first averaged image frame with said second averaged image frame to provide a first difference frame;
      means for enhancing said first difference frame using a linear look-up table to stretch pixel values composing said difference frame;
      means for filtering said stretched difference frame;
      means for compressing said stretched difference frame and for color-coding said compressed difference frame; and
   a monitor for superimposing an image of said color-coded difference frame upon an analog video image of said first or second averaged image frame to provide a composite image for identifying those portions of said cortical area subject to neuronal activity in response to said predetermined input stimuli.

26. Apparatus for optically imaging neuronal activity during neurosurgery comprising:
   means for illuminating a cortical area;
   means for detecting light reflected from aid cortical area; and,
   means for acquiring and analyzing a digitized image obtained from said detected light during neurosurgery to provide on-line identification of those portions of said cortical area where neuronal activity has occurred, wherein said acquiring and analyzing means further includes means for obtaining said digitized image by subtractively combining at least two image frames of data obtained from said reflected light, said two image frames being spatially translated relative to one another.

27. Apparatus according to claim 26, further comprising:
   means for displaying an analog video image of said cortical area; and
   means for superimposing said digitized image on said analog video image of said cortical area to provide a composite image which identifies said cortical area portions where neuronal activity has occurred.

28. Apparatus according to claim 27, wherein aid acquiring and analyzing means updates said composite image in real time during said neurosurgery.

29. Apparatus according to claim 287, wherein said updating occurs at a rate of at least 1/30th of a second.

30. Apparatus for optically imaging cortical activity of a mammalian brain comprising:
   means for detecting light reflected from a cortical area;
   means for storing at least two frames of data obtained from said reflected light; and,
   means for analyzing said at least two frames to identify intrinsic signal changes of said cortical area by spatially translating said at least two frames relative to one another and subtractively combining said at least two frames to provide a difference frame.

31. Apparatus according to claim 30, wherein said difference frame is composed of an array of data elements representative of reflective light intensity differences in said cortical area and said analyzing means identifies an acceptable range of said intensity differences and, stretches said intensity differences in said acceptable range over a larger range of values.

32. Apparatus according to claim 31, wherein said stretching includes linearly stretching said intensity differences in said acceptable range to retain relative differences between said intensity differences.

33. Apparatus according to claim 31, wherein said analyzing means further assigns an intensity value to each data element in said array based on an average of intensities associated with data elements in a predetermined proximity to each data element and, subsequently assigns an intensity value to each data element in said array based on a median value associated with data elements in a predetermined proximity to each data element.

34. Apparatus according to claim 33, wherein said analyzing means further includes:
   means for compressing a range of intensity values used to represent said data elements; and,
   means for color-coding said data elements based on said compressed range of intensity values.

35. Apparatus according to claim 30, wherein said difference frame is composed of an array of data elements representative of reflective light intensity differences in said cortical area, and wherein said analyzing means further includes:
   means for color-coding said difference frame based on said intensity values; and,
   means for superimposing said color-coded difference frame upon an image corresponding to one of said at least two frames.

36. Apparatus according to claim 30, wherein said detecting means, said storing means and said analyzing means dynamically operate in real time.

37. Apparatus according to claim 30, wherein each of said at least two frames is composed of averaged data from a plurality of frames of said detected light.

38. Apparatus according to claim 30, wherein at least one of said at least two frames is obtained during a stimulation period characterized by the presence of a stimulus to a non-cortical part of a patient to evoke a reaction in the cortical area.

* * * * *